(12) United States Patent
Higazi

(10) Patent No.: US 7,271,143 B1
(45) Date of Patent: Sep. 18, 2007

(54) PEPTIDES FOR REGULATION OF UROKINASE (UPA) AND TISSUE TYPE (TPA) PLASMINOGEN ACTIVATOR AND METHOD OF OPTIMIZING THERAPEUTIC EFFICACY

(75) Inventor: Abd. Al-Roof Higazi, Shimshon (IL)

(73) Assignee: Thrombotech Ltd., Nazareth Illit (IL)

( * ) Notice: Subject to any disclaimer, the term of this patent is extended or adjusted under 35 U.S.C. 154(b) by 143 days.

(21) Appl. No.: 10/386,777

(22) Filed: Mar. 12, 2003

Related U.S. Application Data

(63) Continuation-in-part of application No. PCT/US02/02007, filed on Jun. 24, 2002, and a continuation-in-part of application No. 10/063,046, filed on Mar. 14, 2002, and a continuation-in-part of application No. 09/902,135, filed on Jul. 10, 2001, now abandoned.

(51) Int. Cl.
*C07K 1/00* (2006.01)
*C07K 5/00* (2006.01)
*A61K 38/00* (2006.01)

(52) U.S. Cl. .......................... 514/2; 514/834; 530/300; 530/326

(58) Field of Classification Search ............... None
See application file for complete search history.

(56) References Cited

U.S. PATENT DOCUMENTS

| | | | |
|---|---|---|---|
| 4,558,010 A | 12/1985 | Hung et al. | 435/212 |
| 6,150,332 A * | 11/2000 | Wright et al. | 514/16 |

FOREIGN PATENT DOCUMENTS

WO 99/20295 * 4/1999

OTHER PUBLICATIONS

Zhang et al. Regulation of Single Chain Urokinase Binding, Internalization, and Degradation by a Plasminogen Activator Inhibitor 1-Derived Peptide (1997) J. Biol. Chem. 272(43): 27053-27057.*

Simmons M. Cardiol. Clin 1995, 13:339-345, abstract only.

Cipolla M et al., Stroke 2000, 31:940-945.

Higazi, A. A.-R et al., The Journal of Biological Chemistry, 1995, 270:9472-9477.

Wardlaw, J.M. et al., Lancet, 1997, 350:607-614.

Erdem, Y. et al., American Journal of Hypertension, Ltd., 1999, 11:1071-1076.

Adams, David S. et al., The Journal of Biological Chemistry, 1991, 266:8476-8482.

Herz, Joachim, et al., "LRP: a multifunctional scavenger and signaling receptor", J. Clin. Invest., 2001, 108:779-784.

Haj-Yehia, A. et al., "Urokinase-derived peptides regulate vascular smooth muscle contraction in vitro and in vivo", The FASEB Journal, 2000, 14:1411-1422.

Madison, E. L. et al., "Amino acid residues that affect interaction of tissue-type plasminogen activator with plasminogen activator inhibitor 1", Proc. Natl. Acad. Sci. USA 87 (1990), 87:3530-3533.

Madison, E. L. et al., "Restoration of Serine Protease-Inhibitor Interaction by Protein Engineering", The Journal of Biological Chemistry, 1990, 265:21423-21426.

Higazi, A., et al Blood 89: 542-551 (1996).

Higazi A et al J Biol Chem 272: 5348-5353 (1997).

* cited by examiner

*Primary Examiner*—Nashaat T. Nashed
*Assistant Examiner*—Holly Schnizer
(74) *Attorney, Agent, or Firm*—Winston & Strawn LLP

(57) ABSTRACT

Compositions of the polypeptide SEQ ID NO:1, SEQ ID NO:2, anti-LRP antibodies, LRP antagonists, and/or one or more fibrinolytic agents are formulated for enhancing the fibrinolytic activity, reducing the side effects due to vasoactivity caused by the fibrinolytic agents, and/or prolonging the half lives of the fibrinolytic agents. The invention further relates to combination compositions and/or therapy regimens, comprising the polypeptide SEQ ID NO:1 and/or SEQ ID NO:2 and one or more currently used plasminogen activators.

9 Claims, 8 Drawing Sheets

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: synthetic peptide

<400> SEQUENCE: 1

Glu Glu Ile Ile Met Asp
1               5

<210> SEQ ID NO 2
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa=Ac-Arg
<220> FEATURE:
<221> NAME/KEY: Xaa
<222> LOCATION: (18)..(18)
<223> OTHER INFORMATION: Xaa=Arg-amide
```

```
<400> SEQUENCE: 2

Xaa Met Ala Pro Glu Glu Ile Ile Met Asp Arg Pro Phe Leu Tyr Val
1               5                   10                  15

Val Xaa
```

PEPTIDES FOR REGULATION OF UROKINASE (UPA) AND TISSUE TYPE (TPA) PLASMINOGEN ACTIVATOR AND METHOD OF OPTIMIZING THERAPEUTIC EFFICACY

CROSS-REFERENCES TO RELATED APPLICATIONS

This application is a Continuation-in-part of U.S. application Ser. No. 09/902,135 filed on Jul. 10, 2001 now abandoned, entitled "Peptide for Regulation of Tissue Plasminogen Activator"; International Application No. PCT/US02/02007 filed on Jun. 24, 2002, entitled "Peptide for Regulation of Tissue Plasminogen Activator"; and U.S. application Ser. No. 10/063,046 filed on Mar. 14, 2002, entitled "Peptide for Regulation of Urokinase Plasminogen Activator and Method of Optimizing Therapeutic Efficacy", all of which are incorporated in their entirety, by reference herein.

FIELD OF THE INVENTION

This invention discloses a peptide comprising of six amino acids (SEQ ID NO:1) or eighteen amino acids (SEQ ID NO:2) having the property to bind at the "docking" site in urokinase plasminogen (uPA) activator and in tissue type plasminogen activator (tPA) outside the active site. The invention also relates to the regulation of tPA or uPA activity when tPA or uPA is given in treatment of ischemic stroke, in particular to tPA's or uPA's capacity to induce intracerebral hemorrhage (ICH), to the single chain urokinase plasminogen activator (scuPA) to clear blood clots that cause stroke or myocardial infarction.

BACKGROUND TO THE INVENTION

Tissue-type plasminogen activator is the only therapy for the acute thromboembolic stroke, which is approved by the Food and Drug Administration (FDA). However, there is reason for concern that use of tPA for treatment of ischemic stroke may expose patients to secondary intracerebral hemorrhage. Wardlaw J C et al, *Lancet* 1997, 350:607–614. This is because there is an approximately six percent incidence of subsequent symptomatic intracerebral hemorrhage and approximately fifty percent of these patients die. The appearance of intracerebral hemorrhage after treatment with tPA is attributed to its capacity to interfere with the normal vasoactivity of the cerebral blood vessels. TPA has been shown to have dose-dependent vasoconstrictory or vasodilatory effects besides promoting the activation of plasminogen.

Tissue-type plasminogen activator is a naturally occurring molecule released from vascular endothelial cells, and rapid removal of tPA from the blood occurs by clearance in the liver. Hepatocytes express the low-density lipoprotein receptor-related protein or $d_2$-macroglobulin receptor which binds tPA and complexes of plasminogen activator inhibitor (PAI-1) with tPA and tcuPA. Alternately, endothelial cells express a 170 Kda mannose-dependent receptor which is also involved in the rapid clearance of tPA.

Pro-uroldnase (Pro-UK) also known as single chain urokinase plasminogen activator (scuPA), is a naturally occurring molecule released from vascular endothelial cells in response to formation of blood clots and other pathological conditions. ScuPA or Pro-UK can be activated by two different mechanisms a) by cleavage of a single peptide bond by plasmin that leads to the generation of the active form composed of two chains (tcuPA) and b) by binding of scuPA to its receptor, urokinase plasminogen activator receptor (uPAR).

Plasminogen activator inhibitor type 1 (PAI-1) binds to tcuPA and inhibits its catalytic activity. However, PAI-1, which binds tcuPA with high affinity, binds with only low affinity, if at all, to scuPA.

Plasminogen activator inhibitor type 1 interacts with both tPA and uPA and inhibits the catalytic activity of both proteins. PAI-1, which binds tPA and uPA with high affinity is present at high concentrations in the circulation of patients suffering from hypertension. And, reduction of blood pressure by medical treatment results in a decrease of PAI-1 concentrations. The underlying mechanism of action for the increase of PAI-1 in certain pathological conditions is not understood well. However, the inverse relationship with tPA and/or uPA suggests that PAI-1 serves to neutralize in some way the vasoactive effect of tPA and/or uPA. Simmons M, *Cardiol. Clin* 1995, 13:339–345; Cipolla M et al., *Stroke*, 2000, 31:940–945; of PAI-1; and Higazi, A. A.-R et al., *J. Biol. Chem.*, 1995, 270:9472–9477.

The question of whether there is a link between increased levels of PAI-1 concentrations in certain pathological conditions and naturally produced tPA, or whether there is a link between PAI-1 and intracerebral hemorrhage due to use of commercially produced tPA, has not been evaluated heretofore. The present invention is directed to gain a better understanding of the control if any, of PAI-1 or tPA or uPA, and to providing a composition or product optimally effective at regulating activity of tPA or uPA, thereby reducing the risk of intracerebral hemorrhage in patients receiving thrombolytic therapy such as tPA and/or uPA.

Several approaches to thrombolytic therapy have been under investigation, one being through the systemic infusion of activators of the naturally occurring or commercially produced recombinant varieties of fibrinolytic agents. Urokinase is a thrombolytic agent active through the conversion of plasminogen to plasmin. Urokinase is a complex protein of unknown structure which is found in urine in trace amounts. Recombinant forms of urokinase have been developed and are being tested for clinical efficacy, for example U.S. Pat. No. 4,558,010 issued to Abbott Laboratories, describes a recombinant deoxyribonucleic acid which codes for the plasminogen activator protein having human urokinase activity.

The present invention demonstrates that a six amino acid peptide (SEQ ID NO:1) or an eighteen amino acid peptide (SEQ ID NO:2), can reduce the undesirable side effects of fibrinolytic agents, for example, the risk of intracerebral hemorrhage in patients receiving tPA, uPA, tcuPA, streptokinase, rt-PA or alteplase, rt-PA derivatives or anisoylated streptokinase complex. In the protocol employed, the peptide was introduced into the thrombolytic regimen in later stages to prevent the vasoactive or side effects of the primary thrombolytic agent.

The question of whether the peptide has any effect when administered in the early stage of the thrombolytic therapy, has not been investigated heretofore. The present invention describes some unexpected results obtained when the peptide is administered when combined with a plasminogen activator right from the start of the thrombolytic therapy. The results are unexpected because they demonstrate a synergistic effect when the peptide and the plasminogen activator are administered together in in vitro and in in vivo systems. The present invention thus provides novel compositions of different plasminogen activators and the peptide and methods for optimizing the efficacy of thrombolytic agents in combination therapeutic regimens. Such an approach suggests that the effective dosage of the thrombolytic agent can be reduced in the presence of the peptide. This in turn reduces the risk for side effects of these agents, the side effects being manifested in the late stage of therapy.

SUMMARY OF THE INVENTION

The present invention relates to the compositions and use of polypeptides composed of 6 amino acids (SEQ ID NO:1) or 18 amino acids (SEQ ID NO:2), in combination with one or more thrombolytic agents including, but not limited to, scuPA, tPA, uPA, tcuPA, streptokinase, rt-PA or alteplase, rt-PA derivatives (such as reteplase, lanoteplase and TNK-rt-PA), anisoylated plasminogen streptokinase complex (APSC) or anistreplase, or streptokinase derivative.

The present invention relates to the composition and use of a polypeptide composed of 6 amino acids (SEQ ID NO:1) having an inhibitory activity on the vasoactivity of tPA and uPA. The amino acid sequence of this peptide SEQ ID NO:1 is:

Glu-Glu-Ile-Ile-Met-Asp

The present invention also relates to the composition and use of a polypeptide composed of 18 amino acids (SEQ ID NO:2) having an inhibitory activity on the vasoactivity of tPA and uPA. The amino acid sequence of this peptide is:

Ac-Arg-Met-Ala-Pro-Glu-Glu-Ile-Ile-Met-Asp-Arg-Pro-Phe-Leu-Tyr-Val-Val-Arg-Amide Specifically, the polypeptides are useful in enhancing the activity of the thrombolytic agent including, but not limited to, scuPA, tPA, uPA, tcuPA, streptokinase, rt-PA or aeteplase, rt-PA derivatives (such as reteplase, lanoteplase and TNK-rt-PA), anisoylated plasminogen streptokinase complex (APSC) or anistreplase, or streptokinase derivative, and thereby reducing the effective dosage of the thrombolytic agent required in the prevention and/or treatment of thromboembolic disorders.

More specifically, the polypeptides SEQ ID NO:1 and/or SEQ ID NO:2 are useful in the prevention and/or treatment of hemorrhagic disorders associated with tPA treatment administered for treatment of thromboembolic disorders.

Also, contemplated by the present invention are methods of reducing the occurrence of intracerebral hemorrhage in patients receiving tPA or uPA as fibrinolytic therapy, by adjunctive therapy with SEQ ID NO:1 and/or SEQ ID NO:2.

Also, contemplated by the present invention are methods of reducing the occurrence of intracerebral hemorrhage in patients receiving fibrinolytic therapy, including, but not limited to, scuPA, tPA, uPA, tcuPA, streptokinase, rt-PA or aeteplase, rt-PA derivatives (such as reteplase, lanoteplase and TNK-rt-PA), anisoylated plasminogen streptokinase complex (APSC) or anistreplase, or streptokinase derivative.

In yet another embodiment, the present invention is directed to pharmaceutical kits for the treatment of thromboembolic disorders in mammals, the kits comprising a sterile container of a thrombolytic agent including, but not limited to, scuPA, tPA, up.#tcuPA, streptokinase, rt-PA or alteplase, rt-PA derivatives (such as reteplase, lanoteplase and TNK-rt-PA), anisoylated plasminogen streptokinase complex (APSC) or anistreplase, or streptokinase derivative, and one or more of the peptides in commercially available forms, both in amounts therapeutically effective to treat the thromboembolic disorders.

In yet another embodiment, the present invention is directed to pharmaceutical kits for the treatment of thromboembolic disorders in mammals, the kits comprising a sterile container of tPA in commercially available forms, and a sterile container of SEQ ID NO:1 or SEQ ID NO:2, both in amounts therapeutically effective to treat the thromboembolic disorders, while in the same regimen, preventing the occurrence of side effects of tPA.

The foregoing kits may include, thrombolytic agents if desired, including, but not limited to, scuPA, tPA, uPA, tcuPA, streptokinase, rt-PA or alteplase, rt-PA derivatives (such as reteplase, lanoteplase and TNK-rt-PA), anisoylated plasminogen streptokinase complex (APSC) or anistreplase, or streptokinase derivative, in amounts therapeutically effective to treat thromboembolic disorders as well as prevent any side effects.

The foregoing kits may include, if desired, uPA and the SEQ ID NO:1 and/or SEQ ID NO:2 in amounts therapeutically effective to treat thromboembolic disorders as well as prevent any side effects.

It is also within the scope of this invention to provide kits, where appropriate, of combinations of two or more thrombolytic agents along with the peptide. It is further the object of the present invention to provide methods of treating thromboembolic disorders using a conjunctive therapy in combination with one or more of fibrinolytic agents including scuPA, tPA, uPA, tcuPA, streptokinase, rt-PA or alteplase, rt-PA derivatives (such as reteplase, lanoteplase and TNK-rt-PA), anisoylated plasminogen streptokinase complex (APSC) or anistreplase, or streptokinase derivative, the method comprising of administering the combination therapy right from the start of the regimen.

It is also within the scope of this invention to provide kits of tPA or uPA in combination regimens of other fibrinolytic agents, along with SEQ ID NO:1 and/or SEQ ID NO:2 where appropriate. It is further the object of the present invention to provide methods of treating thromboembolic disorders using SEQ ID NO:1 and/or SEQ ID NO:2 as conjunctive therapy in combination with one or more of fibrinolytic agents including tPA, uPA, tcuPA streptokinase, rt-PA or alteplase, rt-PA derivatives (such as reteplase, lanoteplase and TNK-rt-PA), anisoylated plasminogen streptokinase complex (APSC) or anistreplase, or streptokinase derivative.

BRIEF DESCRIPTION OF THE FIGURES

The advantages and features of the present invention will become readily apparent after reading the following detailed description and referencing the drawings, which are.

DETAILED DESCRIPTION OF THE INVENTION

Figure 1A:
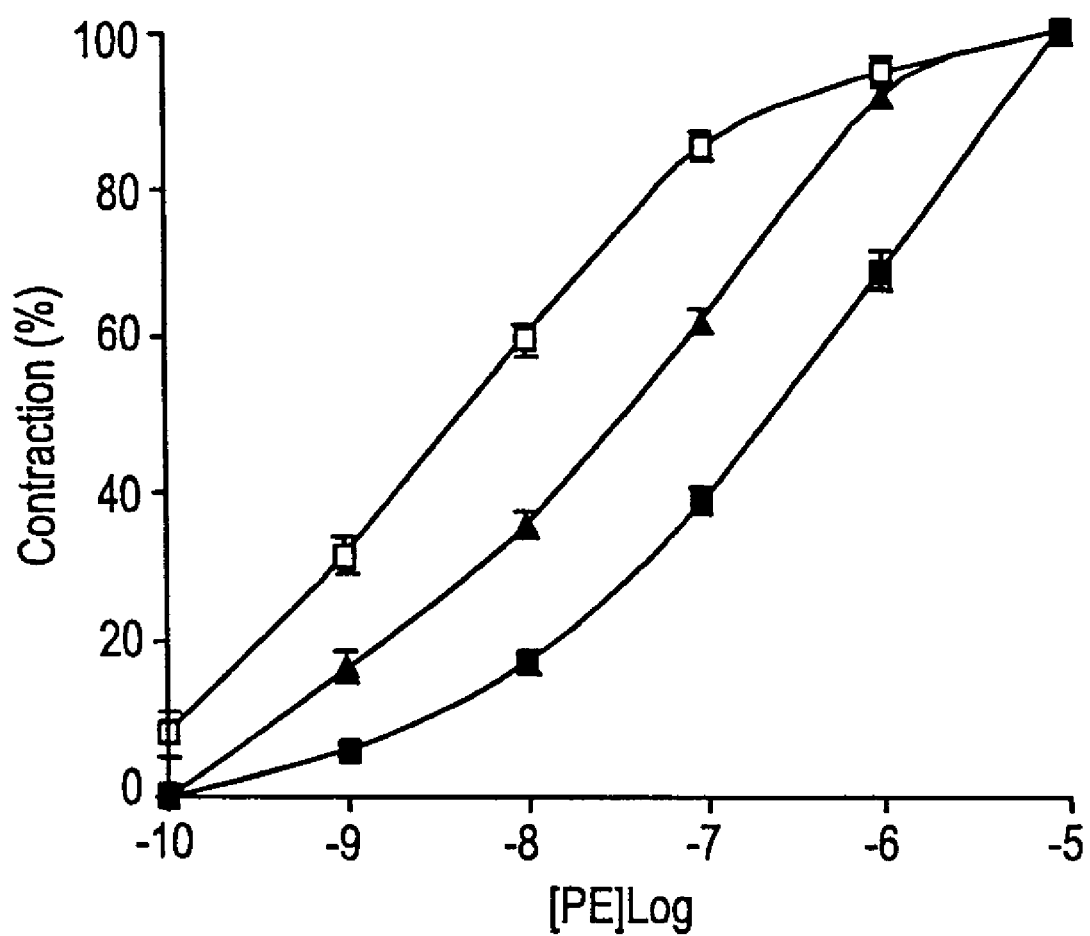
FIG. 1A is a diagram describing the results of experiments on the effect of tPA on PE-induced contraction of isolated rat aorta rings. Contraction of aortic rings was induced by increasing the concentrations of phenylephrine (PE), in the absence of tPA (full triangles) or in the presence of 1 nM (filled squares) or 20 nM tPA (empty squares).

In accordance with the present invention, pharmaceutical compositions of the peptides SEQ ID NO:1 and/or SEQ ID NO:2 are provided, such compositions having inhibitory effects on tPA and/or uPA related hemorrhagic disorders that result as serious side effects of such fibrinolytic agents. Also, contemplated by the present invention are methods of reducing the occurrence of intra-cerebral hemorrhage in patients receiving tPA or uPA in the treatment of thromboembolic disorders.

The present invention also provides pharmaceutical compositions and kits comprising of the polypeptide SEQ ID NO:1 and/or SEQ ID NO:2, in combination with one or more of fibrinolytic agents including tPA, uPA, tcuPA, streptokinase, rt-PA or alteplase, rt-PA derivatives (such as reteplase, lanoteplase and TNK-rt-PA), anisoylated plasminogen streptokinase complex (APSC) or anistreplase, or streptokinase derivatives.

The present invention also provides methods for improving the efficacy of fibrinolytic agents, thereby reducing the effective dosage, by combining the fibrinolytic agent with the peptide, in a ratio of 0.1/1.0 to 1.0/0.1 respectively.

The present invention further provides methods for preventing and/or treating side effects such as intracerebral hemorrhage and related vascular abnormalities associated with fibrinolytic agents such as tPA or uPA, by providing therapeutic regimens—solo or in combination, in combination with an effective amount of SEQ ID NO:1 and/or SEQ ID NO:2 to prevent and/or inhibit side effects.

TPA is a single-chain serine protease composed of 530 amino acids, although originally 527 were identified. The t-PA enzyme is composed of several domains with homologies to other proteins:

A finger domain comprising residues 4–50,
A growth factor domain comprising residues 50–87,
two kringles comprising residues 87–176 and 176–262, and the protease domain constituted by residues 276–527 comprising the catalytic triad. Binding of tPA to fibrin is most likely mediated via the finger and the second kringle domains. Initial binding of t-PA to fibrin is governed by the finger domain and by kringle 2, which binds to exposed carboxyl-terminal lysine residues.

TPA has a weak affinity for plasminogen in the absence of fibrin (Km–76 uM but a much higher affinity in the presence of fibrin (K between 0.15 and 1.5 uM). In this reaction plasminogen binds to fibrin primarily via specific structures called the "lysine-binding site." Thus one way of regulating fibrinolysis is at the level of plasminogen activation localized at the fibrin surface.

Plasminogen activator inhibitors, specifically PAI-1 and PAI-2 inhibit the physiological plasminogen activators, for example, PAI-1 is the primary inhibitor of t-PA and u-PA in plasma PAI-1, a serine protease inhibitor, is a single chain glycoprotein derived from endothelial cells and other cell types. PAI-1 inhibits tPA by the formation of a complex between the active site of tPA and the "bait" residues (Arg 346-Met 347) of PAI-1.

The PAI-1 concentration in plasma is increased in several diseases, including venous thromboembolism, obesity, sepsis and coronary artery disease. High PAI-1 activity constitutes an independent risk factor for myocardial infarction in young subjects within three (3) years of the first attack. There is a clear correlation between the circadian variation in the time of onset of myocardial infarction, with the highest incidence at about 8 am and the circadian rhythm of plasma PAI-1 activity which is also highest early in the morning.

Plasminogen activator inhibitor type I interacts with both tPA and uPA and inhibits the catalytic activity of both proteins. PAI-1, which binds to tPA and uPA with high affinity (Heckman C M, Archives of Biochem Biophysics, 1988, 262:199–210), is also present at high concentrations in the circulation of patients suffering from hypertension. Reduction of blood pressure by medical treatment results in the decrease of PAI-1 concentration. Erden Y C et al. *Am J Hypertens*, 1999, 12:1071–1076. The underlying mechanism of action to explain the increase of PAI-1 in some pathological conditions is not understood.

PAI-1 reacts with single chain tPA, two chain tPA and tcuPA. The second-order rate constant for their inhibition of single-chain tPA by PAI-1 is about $10^7$ M-'$_s$, while inhibition of two chain tPA and tcuPA is somewhat faster. Positively charged regions in tPA (residues 296–304) and uPA (residues 179–184) are involved in this rapid reaction. PAI activity is very rapidly cleared from the circulation by the liver. Except for platelets, which contain both functional and inactive PAI-1, PAI-1 is not stored within cells, but is rapidly and constitutively secreted after synthesis.

PAI-1 binds tPA and uPA through two independent epitopes, one of which interacts with the active site. The other epitope is composed of 6 amino acid residues, SEQ ID NO:1 that correspond to the amino acid residues 350 to 355 of PAI-1. This second epitope of PAI-1 interacts with a binding "docking" site in uPA and tPA that is outside of the active site. Adams D S et al., *J. Biol. Chem,* 1999, 266: 8476–8482.

scuPA

The present invention describes the effect of the 6 amino acid peptide on the fibrinolytic activity of scuPA and indicates that the peptide stimulates synergistically the activity of scuPA on blood clot lysis. These observations are described in detail in the Examples section.

The peptide of the present invention, while preventing and/or inhibiting the adverse effects of scuPA on blood vessels, has no effect on the fibrinolytic activity of scuPA. The peptide is therefore useful in clot lysis during thrombolytic therapy in myocardial infarction, stroke and related complications.

The commercially available tPA is produced by recombinant DNA technology (such as recombinant t-PA, rt-PA) in two forms: a single-chain preparation (alteplase) and a double-chain preparation (dute plase). Other tPA types include reteplase (r-PA) and a mutant of rt-PA, TNK-rt-PA. See below for details under section entitled "TNK-tPA and rtPA".

The preferred dosage regimen of fibrin-selective alteplase consists of a weight-adjusted accelerated (front-loaded) regimen over 90 minutes (15 mg bolus, 0.75 mg/kg over 30 minutes (not to exceed 50 mg) and 0.05 mg/kg over 60 minutes [not to exceed 35 mg]). The present invention provides a composition of alteplase and the peptide, such that the level of fibrinolytic activity achieved in above dosage regimen is actually obtained with much lower dosage of alteplase. This is because the combination of alteplase and the peptide results in better lysis activity.

The above improvement is also observed when the preferred dosage regimen of fibrinselective alteplase consists of a weight-adjusted accelerated (front-loaded) regimen over 90 minutes (15 mg bolus, 0.75 mg/kg over 30 minutes [not to exceed 50 mg] and 0.05 mg/kg over 60 minutes [not to exceed 35 mg]).

The preferred dosage regimen for the peptide consists of an amount effective to optimally enhance the activity of the fibrinolytic activity while also preventing the harmful vasoactive effects of a fibrinolytic agent on a case by case basis. The peptide may be a component of a sequence of varying numbers of amino acids, or the peptide may have a modification of one or more amino acids in its sequence. The ratio of peptide/tPA, UPA, or TNK-tPA maybe in the range of 0.1/1.0 to 1.0/0.1.

The peptide of the present invention is useful in treatment of sepsis, when administered alone in an effective dosage or in combination with traditional anti-coagulant therapy. Under physiological conditions, several antithrombotic mechanisms act in concert to prevent clotting, and to preserve blood fluidity. Any thrombin that escapes the surveillance of this physiological anticoagulant system is available to convert fibrinogen to fibrin. This in turn triggers the fibrinolytic system.

tPA

The present invention describes the effect of the peptide on the vasoactivity of tPA and uPA and indicates that the peptide abolishes the enhancing effect of tPA on phenylephrine-induced vasoconstriction in aorta ring cultures. Similarly, the peptide of the present invention abrogates the enhancing effect of uPA on phenylephrine-induced vasoconstriction. These observations are described in detail in the Examples section.

The SEQ ID NO:1 and/or SEQ ID NO:2 peptides of the present invention, while preventing and/or inhibiting the adverse effects of tPA or uPA on blood vessels has no effect on the fibrinolytic activity of tPA or uPA, so useful in clot lysis during thrombolytic therapy in myocardial infarction, stroke and related complications.

The commercially available tPA is produced by recombinant DNA technology (such as recombinant t-PA, rt-PA) in two forms: a single-chain preparation (alteplase) and a double-chain preparation (dute place). Other tPA types include reteplase (r-PA) and a mutant of rt-PA, TNK-rt-PA.

The preferred dosage regimen of fibrin-selective alteplase consists of a weight-adjusted accelerated (front-loaded) regimen over 90 minutes (15 mg bolus, 0.75 mg/kg over 30 minutes [not to exceed 50 mg] and 0.05 mg/kg over 60 minutes [not to exceed 35 mg]).

The preferred dosage regimen for the peptide consists of an amount effective to prevent the harmful vasoactive effects of tPA on a case by case basis. The peptide may be a component of a sequence of varying numbers of amino acids, or the peptide may have a modification of one or more amino acids in its sequence.

The peptide of the present invention is useful in treatment of sepsis, when administered alone in an effective dosage or in combination with traditional anti-coagulant therapy. Under physiological conditions, several antithrombotic mechanisms act in concert to prevent clotting, and to preserve blood fluidity. Any thrombin that escapes the surveillance of this physiological anticoagulant system is available to convert fibrinogen to fibrin. This in turn triggers the fibrinolyte system.

TNK-tPA and rtPA

T-PA consists of five domains: a fibronectin finger-like domain, an epidermal growth factor domain (EGF), two kringle domains (K1 and K2), and a protease domain. TNK-t-PA differs from rtPA in the K1 and protease domains. In K1 the glycosylation site at amino acid 117 (N117) has been shifted to amino acid 103, while in the protease domain there is a tetra-alanine substitution (K296A/H297A/R298A/R299A) in the plasminogen activator inhibitor-1 (PAI-1) docking site that makes it resistant to inactivation by PAI-1.

TNK-tissue plasminogen activator (TNK-tPA) is a bioengineered variant of tissue-type plasminogen activator (t-PA), having a longer half-life than tPA. It is resistant to inactivation by plasminogen activator inhibitor-1 on account of having a tetra-alanine substitution in the protease domain (K296A/H297A/R298A/R299A).

TNK-tPA exhibits 80-fold higher resistance to plasminogen activator inhibitor-1 (PAI-1) than tPA and 14 fold greater relative fibrin specificity.

In vitro, TNK-tPA is 8 and 13 fold more potent than tPA towards whole blood and platelet-enriched clots, respectively.

In vivo, the time required by TNK-tPA for 50% lysis in arterial venous shunt models of fibrinolysis in rabbits, was only one third of that required by rtPA. In spite of these enormous advantages of TNK-tPA over TA in experimental situations, TNK-tPA has no significant advantage over TA in clinical studies.

In comparative clinical trials, TNK-tPA is found to have equivalent efficacy to rtPA and with rate of intracranial hemorrhage similar to that with rtPA. The unique significant advantage of TNK-tPA over rtPA is the fact that TNK-tPA is associated with fewer non-cerebral bleeding episodes (4.66% vs. 5.94%).

The present invention elucidates the basis of the discrepancy between the in vitro effects of TNK-tPA and the in vivo effects in humane. Specifically, the effects of TNK-tPA, rtPA and/or tPA were examined on the PE-induced contraction of isolated rings. Results obtained are described in detail below in the section on EXAMPLES. Briefly, results obtained indicate that rtPA has two binding epitopes that are involved in vasoactivity. The fast epitope has greater affinity (around 1 nM) and inhibits the PE induced vasoconstriction. The second epitope has a lower affinity (around 20 nM) and stimulates the PE-induced vasoconstriction. The present invention also suggests that the fast epitope that induces prodilatation, has been inactivated in TNK-tPA.

Results obtained in the present invention indicate that the vasoactive effect of TNK-tPA is unaffected by equimolar concentration of PAI-1 peptide. However, at 5 molar concentration of the peptide, the vasoactive effect of TNK-tPA was abolished. Thus, results described in the EXAMPLES suggest that the PAI-1 derived hexapeptide SEQ ID NO:1 is useful for inhibiting the vasoactive effects of tPA, rtPA and/or TNK-tPA. Similar results were obtained with SEQ ID NO:2 (results not presented).

TPA and LRP

TPA is known to bind (Strickland JHaDK.LRP: a multifunctional scavenger and signaling receptor. *J. Clin. Invest.* 2001; 108:779–784) LRP. This binding is regulated by PAI-1. Results obtained in the present invention demonstrate that LRP is also involved in the vasoactivity of tPA (see below for details in section on EXAMPLES).

Specifically, anti-LRP antibodies and the LRP antagonist, recombinant receptor associated protein, rRAP, both abolished the vasoactive effect of tPA and TNK-tPA. Results described in the present invention suggest that the anti-LRP antibodies and/or rRAP prolong the half-life of tPA in the circulation. These results also suggest that anti-LRP antibodies and/or RAP may be used to prolong the half-life of scuPA or scuPA/suPAR complex (described in a copending U.S. application Ser. No. 09/325,917, filed Jun. 4, 1999; Ser. No. 09/968,752, filed Oct. 2, 2001; Ser. No. 09/302,392, filed Jul. 10, 2001; and Ser. No. 09/902,135, filed Jul. 10, 2001; and incorporated herein, by reference, in its entirety.)

EXAMPLE 1

The effect of TNK-tPA on PE-induced contraction was compared with the effect of tPA, in the isolated aorta rings. The experimental procedure followed has been described earlier (Haj-Yehia A, Nassar T, Sachais B, Kuo A, Bdeir K., Al-Mehdi A-B, Mazar A, Cines D, Higazi A A-R. Urokinase-derived peptides regulate vascular smooth muscle contraction in vitro and in vivo. *FASEB J* 2000; 14:1411–1422.

Figure 1B:
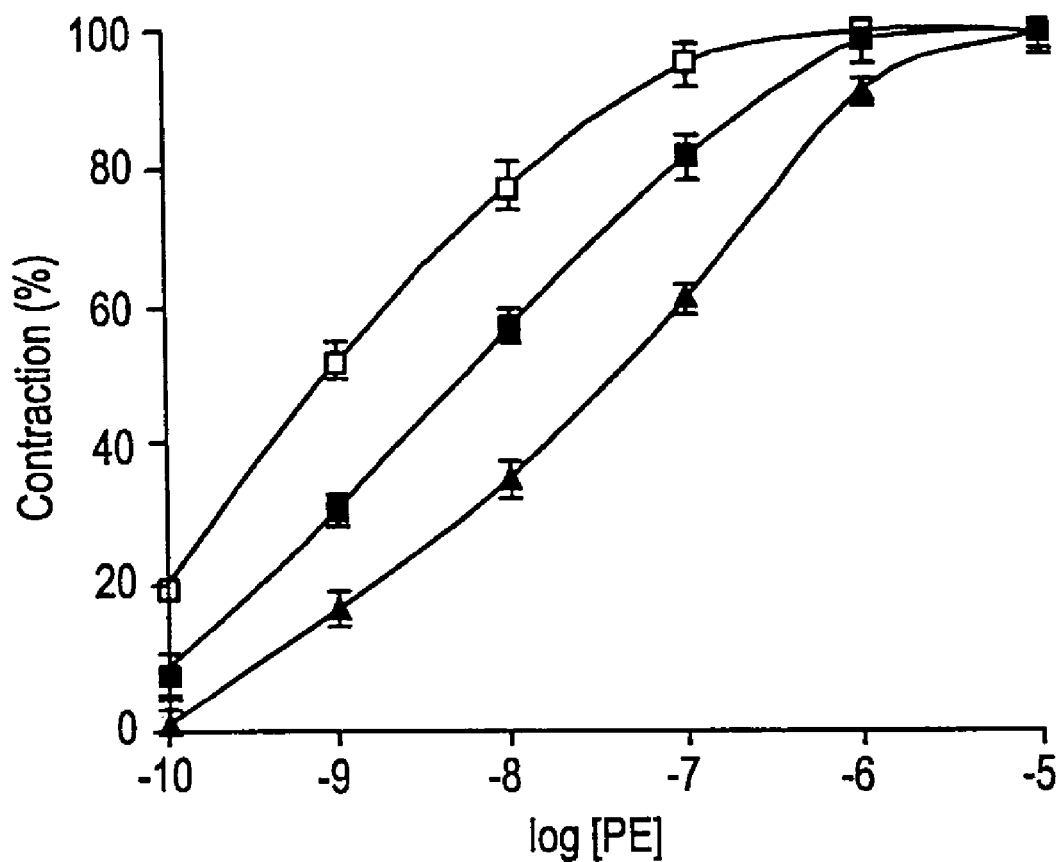
FIG. 1B describes the results of experiments in which the contraction of aortic rings was induced in the absence of TNK-tPA (filled triangles), in the presence of 1 nM tPA (filled squares) or 20 nM tPA (empty squares).

FIG. 1A shows that 1 nM tPA inhibited PE-induced vasoconstriction. FIG. 1B shows that at the same concentration (1 nM) TNK-tPA exerted an opposite effect to that of tPA on the contraction of aorta rings. 1 nM of TNK-tPA stimulated the vasoconstriction induced by PE.

Since the concentration of tPA used in the previous experiments was in the physiological range, but was much below the therapeutic range, the effect of higher concentrations of tPA variants on vasoactivity was examined FIG. 1A shows that increasing the concentration of rtPA produced a similar effect to that induced by 1 nM TNK-tPA. 20 nM of rtPA stimulated the constriction induced by PE and the EC50 was decreased from 34 to 1.6 nM.

FIG. 1B shows that increasing the concentration of TNK-tPA from 1 to 20 nM increased its stimulatory effect on PE-induced vasoconstriction, by decreasing its EC50 from 34 to 0.63 nM.

EXAMPLE 2

Figure 2:
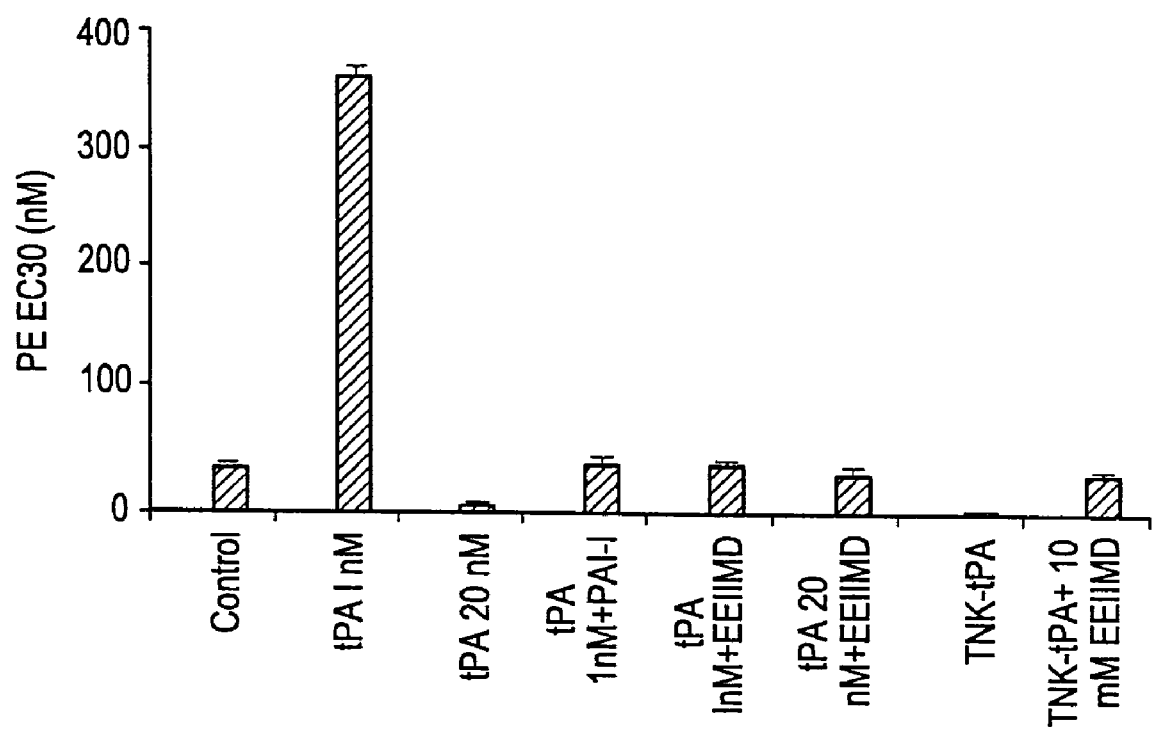
FIG. 2 is a graphical representation of the results obtained in experiments to study the effect of PAI-1 on the vasoactivity of tPA. The EC50 of PE was determined in the absence (Control) or presence of 1 nM tPA, 20 nM tPA, 1 nM tPA and an equimolar concentration of PAI-1, 20 nM tPA and an equimolar concentration of PAI-1, 1 nM tPA and 2 µM of SEQ ID NO:1 or 20 nM tPA and 2 µM of SEQ ID NO:1.

In an attempt to understand the basis for the modification in the vasoactivity of TNK-tPA, the role of the PAI-1 docking site in the process was examined. FIG. 2 shows that the rtPA provasodilatation as well as pro-vasoconstrictive effects are inhibited by equimolar concentrations of PAI-1.

PAI-1 interacts with tPA through independent sites; the catalytic site and a docking site, present in the amino acids 2196 to 299. The PAI-1 docking site is mutated in TNK-tPA. To examine in greater detail the role of the PAI-1 docking site in the vasoactivity of TNK-tPA specifically and of rtPA in general, we examined the effect of the PAI-1 derived hexapeptide SEQ ID NO:1 that correspond to the amino acid residues 350 to 355 of PAI-1 (the epitope in PAI-1 that interacts with the tPA docking site (Madision E L, Goldsmith E J, Gerard R D, Getbing M J H, Sambrook J F, Bassel-Duby R S. Amino acid residues that affect interaction of tissue plasminogen activator with plasminogen activator inhibitor 1. *Proceedings of the National Academy of Science*, USA. 1990; 873530–3534. Madison E L, Goldsmith W. Gething M-J, H., Sambrook J F, Gerard R D. Restoration of serine protease-inhibitor interaction by protein engineering. *Journal of Biological Chemistry*. 1990; 265:21423–21426.

FIG. 2 shows that a concentration of 2 µM, the PAI-1 derived peptide abolished the vasoactive effects of rtPA. Interestingly, the vasoactive effect of TNK-tPA was unaffected by 2 µM concentration of PAI-1 peptide. However, at 10 µM, the peptide abolished the effect of TNK-tPA.

The present invention therefore provides a means of inhibiting the vasoactivity of both tPA and TNK-tPA by combining them with an effective amount of the PAI-1 peptide. Similar results were obtained with SEQ ID NO:2 (results not presented).

EXAMPLE 3

Figure 3:
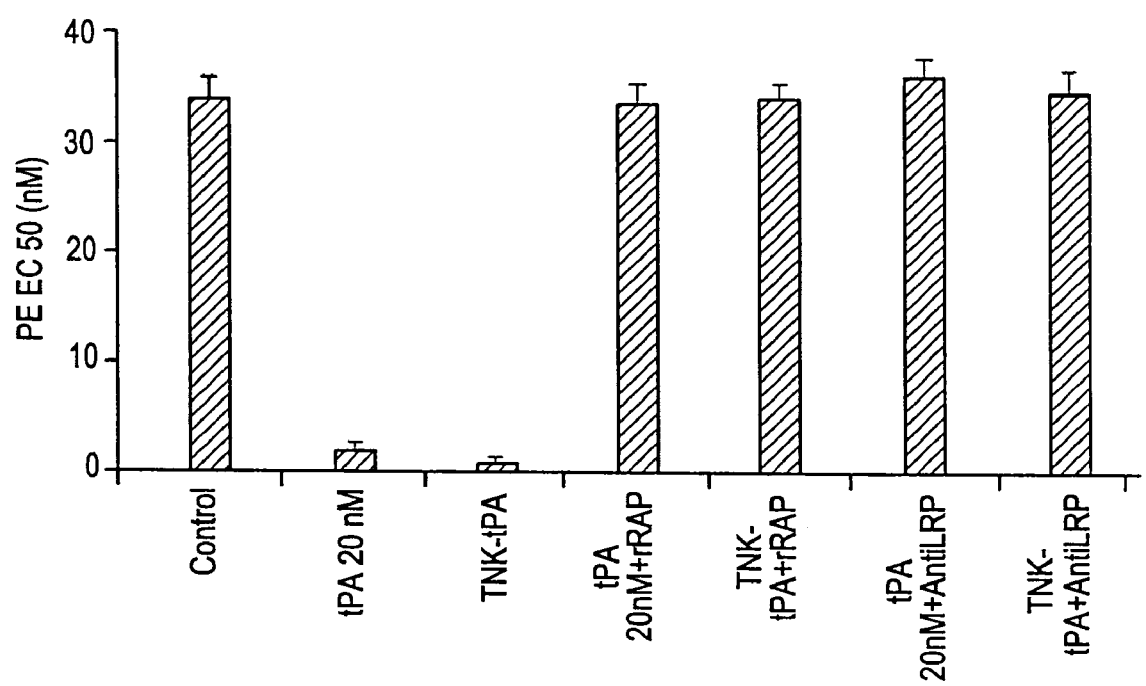
FIG. 3 is a graphical representation of the results obtained in experiments to study the effect of RAP and anti-LRP antibodies on the vasoactivity of tPA. The EC50 of PE was determined in the absence (Control) or presence of 1 nM tPA, 20 nM tPA, 1 nM tPA and an equimolar concentration of PAI-1, 20 nM tPA and an equimolar concentration of PAI-1, 1 nM tPA and 2 μM of SEQ ID NO:1 or 20 nM tPA and 2 μM of SEQ ID NO:1.

The effect of revertase and TNK-tPA on the PE induced vasocontraction was studied in presence or absence of the LRP antagonist (RAP) or anti LRP antibodies. The results obtained shown in FIG. 3, indicate that the vasoactive effect of tPA and/or TNK-tPA is totally abolished by the anti-LRP antibodies as well as by the LRP antagonist rRAP.

EXAMPLE 4

Effect of tPA on Phenylephrine Induced Contraction

Figure 4:
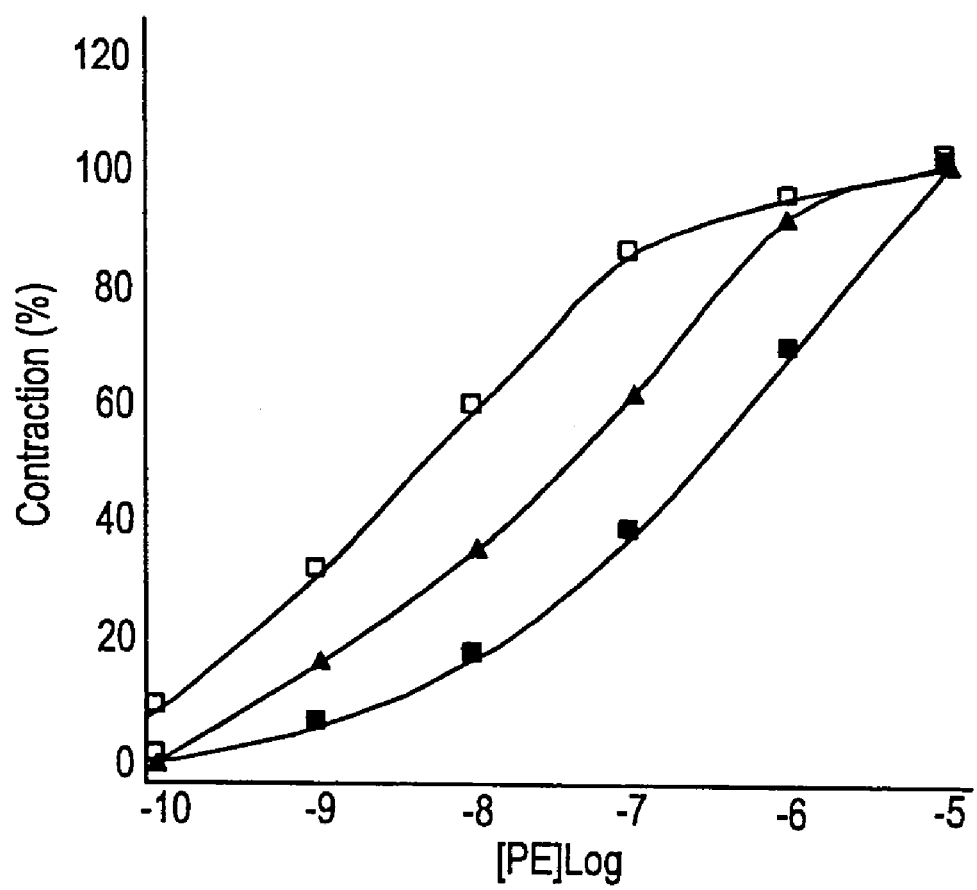
FIG. 4 is a graph describing the effect of tPA on phenylepbrine-induced contraction of isolated rat aorta rings in vitro. The contraction of the aorta rings was induced by varying concentrations of phenylephrine in the absence of tPA (filled triangles), in the presence of 1 nM of TA (filled squares) or in the presence of 10 nM tPA (empty squares). The experiments were performed according to procedures described earlier by Haj-Yehia A et al., FASEB J, 2000, 14:1411–1422.

FIG. 4 describes a graph describing the effect of TA on phenylephrine-induced contraction of isolated rat aorta rings in vitro. The contraction of the aorta rings was induced by varying concentrations of phenylephrine in the absence of tPA (filled triangles), in the presence of 1 nM of tPA (filled squares) or in the presence of 10 nM TA (empty squares). The experiments were performed according to procedures described earlier by Haj-Yehia A et al., *FASEB J,* 2000, 14:1411–1422.

Results obtained confirm that tPA has the capacity to induce vasodilatation.

FIG. 4 shows that the presence of 1 nM TA inhibits the vasoconstriction induced by phenylephrine. Increased tPA concentrations induced the opposite effect, i.e., the presence of 1 nM tPA stimulated the vasoconstriction induced by phenylepbrine. Similarly uPA has the capacity to induce vasodilatation (Haj-Yehia A., et al. *FASEB J,* 2000, 14:1411–1422).

EXAMPLE 5

Effect of PAI-1 on Vasoactivity of uPA and tPA

Figure 5:
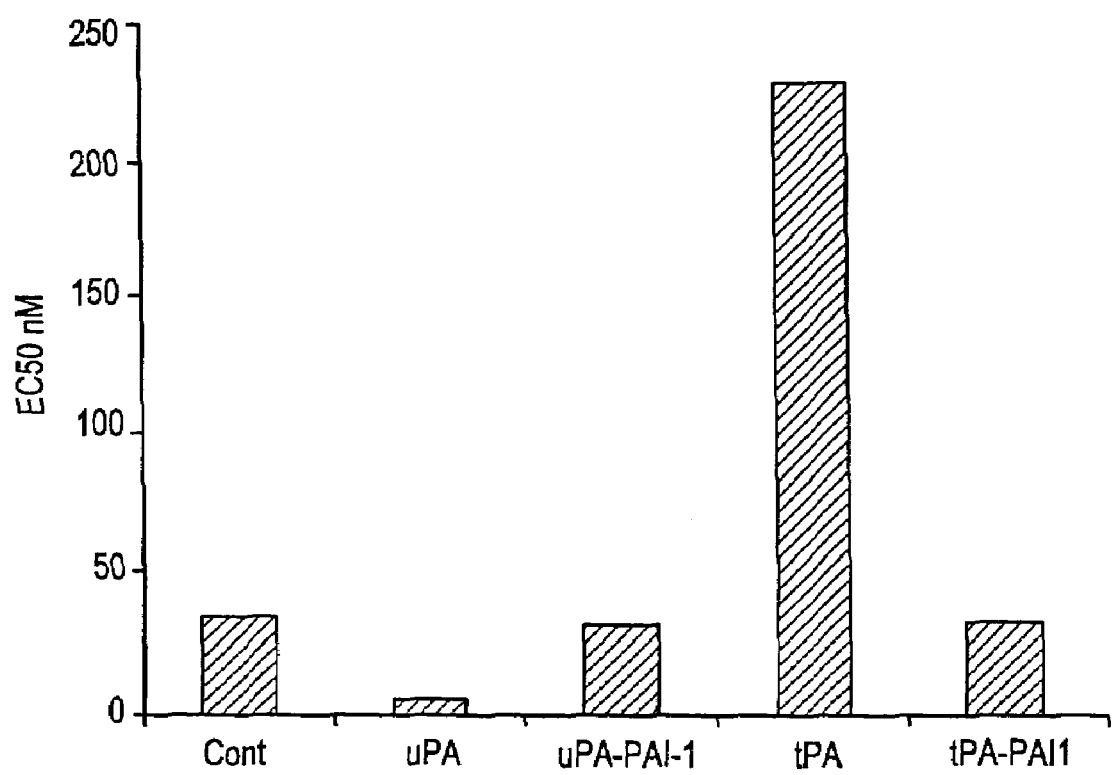
FIG. 5 is a bar diagram describing the results of experiments on the vasoactivity of uPA and tPA in the presence or absence of PAI-1, for example, the effect of 2 nM uPA or 1 nM tPA on phenylephrine induced vasoconstriction was determined in the presence or absence of equimolar concentrations of PAI-1.

FIG. 5 describes a bar diagram describing the results of experiments on the vasoactivity of uPA and tPA in the presence of absence of PAI-1, for example, the effect of 2 nM uPA or 1 nM tPA on phenylephrine induced vasoconstriction was determined in the presence or absence of equimolar concentrations of PAI-1.

EXAMPLE 6

Figure 6:
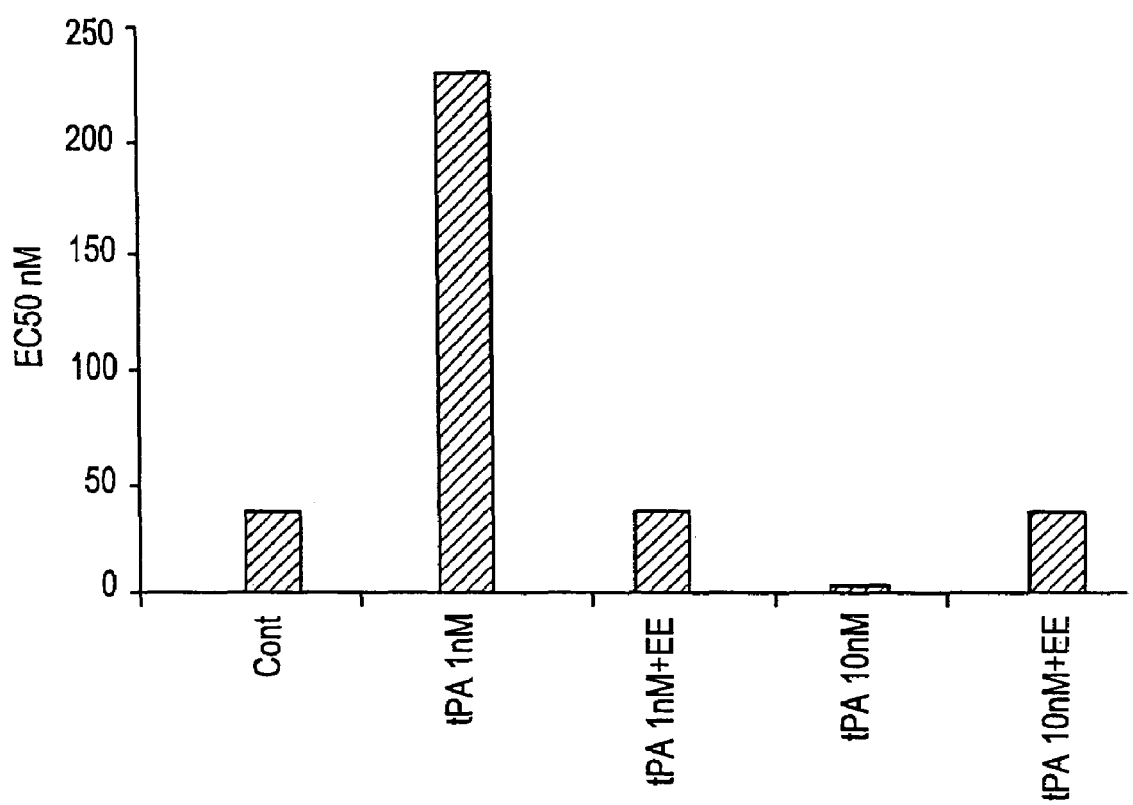
FIG. 6 is a bar diagram describing the results of studies done on the effect of PAI-1 derived peptide on tPA vasoactivity. The constriction of aorta rings was induced by increasing the concentrations of phenylepbrine in the absence or presence of 1 nM tPA, 1 nM tPA and 1 OM SEQ ID NO:1, 10 mM tPA or 10 nM tPA and 1 OM of SEQ ID NO:1.

FIG. 6 is a bar diagram describing the results of studies done on the effect of PAI-1 derived peptide on tPA vasoactivity. The constriction of aorta rings was induced by increasing the concentrations of phenylephrine in the absence or presence of 1 nM tPA, 1 nM tPA and 1 OM, 10 nM tPA or 10 nM tPA and 1 OM.

Results obtained show that 10M of abolished the enhancing effect of tPA on phenylephrine induced vasoconstriction. exerted the same effect on uPA. Neither PAI-1 nor alone had any effect on contraction of aorta rings FIG. 3. Therefore, the mechanism through which PAI-1 affects the vasoactive effect of tPA or uPA is through its interaction with the docking site.

EXAMPLE 7

Effect of PAI-1 Derived Peptide SEQ ID NO:1 on tPA Medicated Clot Lysis

Figure 7:
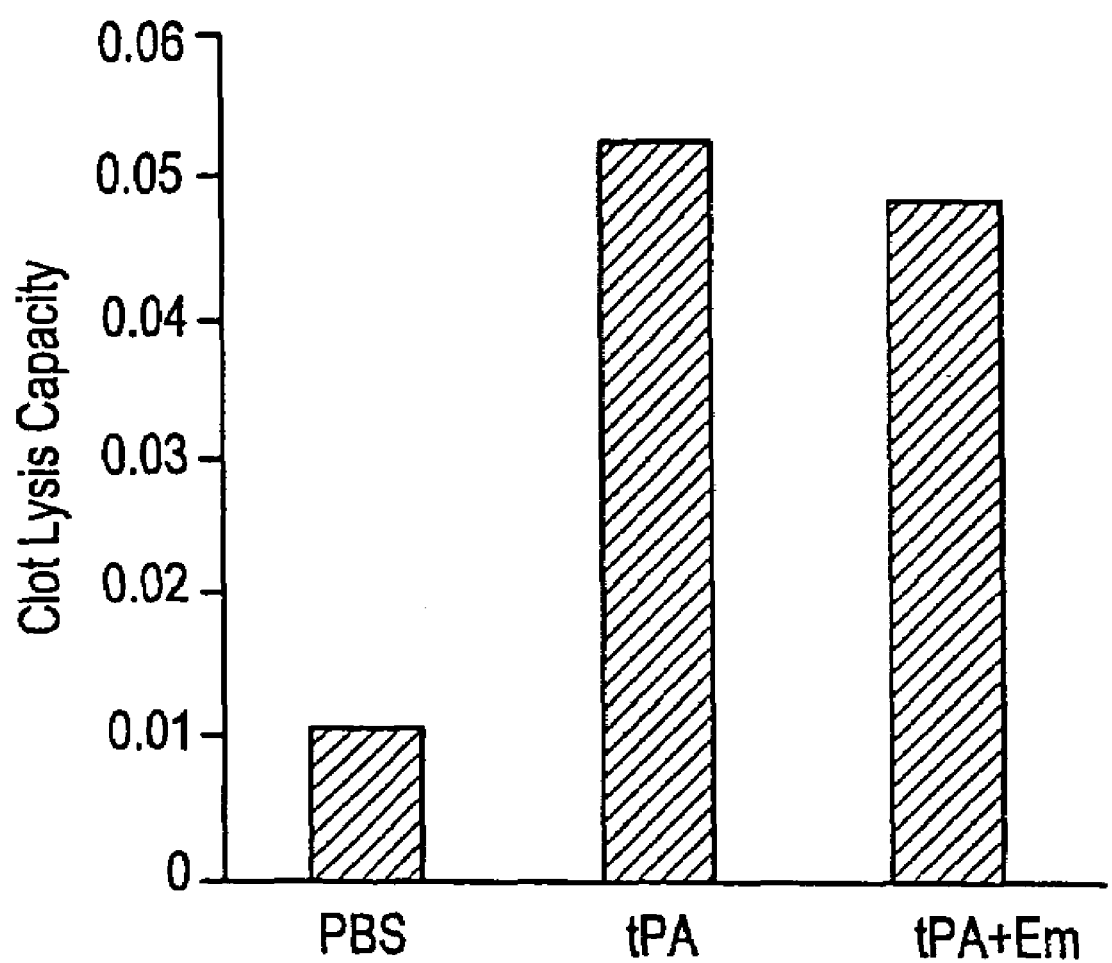
FIG. 7 is a bar diagram describing the results of experiments on the effect of PAI-1 derived peptide on tPA mediated clot lysis. The capacity of TA to induce clot lysis was determined in the presence and absence of 1 OM of SEQ ID NO:1. In these experiments, blood from volunteers was allowed to clot at room temperature for one hour, the blood clot was separated from the plasma, placed on absorbing paper to remove all the serum and cut into several pieces. The pieces were weighed, and placed in PBS buffer alone or containing 100 nM tPA, with or without 1 OM of SEQ ID NO:1. After incubation for 3 hours at room temperature, the thrombi are separated from the medium, dried and weighed.

FIG. 7 is a bar diagram describing the results of experiments on the effect of PAI-1 derived peptide on tPA mediated clot lysis. The capacity of tPA to induce clot lysis was determined in the presence and absence of 10 M. In these experiments, blood from volunteers was allowed to clot at room temperature for one hour, the blood clot was separated from the plasma, placed on absorbing paper to remove all the serum and cut into several pieces. The pieces were weighed, and placed in PBS buffer alone or containing 100 nM tPA, with or without 10M. After incubation for 3 hours at room temperature, the thrombi are separated from the medium, dried and weighed.

Two methods were used to determine whether the peptide affected the fibrinolytic activity of tPA by inhibiting plasminogen activity: 1) The chromogenic assay described in detail earlier (Higazi A. A.-R, et al. *J. Biol. Chem.,* 1995, 270:9472–9477); and 2) The clots lysis test described earlier (Higazi A A-R et al., *Blood* 1988, 92:2075–2083).

Results obtained show that had no significant effect on the catalytic activity of the tPA (FIG. 7).

Therefore, these data indicate that the PAI-1 derived peptide SEQ ID NO:1 (and/or SEQ ID NO:2, results not presented) and their derivatives can neutralize the vasoactivity of tPA or uPA, thereby reducing their adverse effects on blood vessels and preventing the complications that appear during thrombolytic therapy as in the case of myocardial infarction, stroke and similar diseases.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A polypeptide, having an inhibitory effect on vasoactivity induced by plasminogen activators, wherein said polypeptide is Ac-RMAPEEIIMDRPFLYVVR-amide (SEQ ID NO: 2).

2. The polypeptide according to claim 1, wherein the plasminogen activators includes tcuPA, tPA, streptokinase, rt-PA, rt-PA derivatives, APSC, recombinant scuPA prourokinase or the covalent cross linked scuPA/suPAR complex.

3. A composition comprising an effective amount of the polypeptide according to claim 1 to reduce hemorrhage caused by a fibrinolytic agent.

4. The composition according to claim 3, further comprising a fibrinolytic agent selected from the group consisting of scuPA, tPA, uPA, tcuPA, streptokinase, rt-PA, alteplase, rt-PA derivatives, reteplase, lanoteplase, TNK-rt-PA, anisoylated plasminogen streptokinase complex, anistreplase, or a streptokinase derivative.

5. A method of enhancing the fibrinolytic activity of a fibrinolytic agent by administering an effective amount of the polypeptide according to claim 1 and a fibrinolytic agent to induce the desired level of fibrinolytic activity without causing hemorrhage.

6. A method of fibrinolytic therapy in a patient in need thereof, said method comprising administering to the patient a thrombolytic dosage of a thrombolytic agent and thereafter administering an effective supplemental dosage of the polypeptide according to claim 1 in an amount that reduces hemorrhage or side effects, said supplemental dosage of the polypeptide being administered once every 1 to 10 days for the duration of the therapy.

7. The method of fibrinolytic therapy according to claim 6, wherein the thrombolytic agent includes tPA or uPA and is administered at a standard clinical thrombolytic dosage.

8. The method of fibrinolytic therapy according to claim 6, wherein the supplemental dosage of the polypeptide is a bolus up to 500 mg.

9. A method of reducing hemorrhage in a patient receiving said method comprising administering to the patient once every 1 to 10 days a bolus of an amount of the polypeptide according to claim 1, wherein said polypeptide subsequently inhibits vasoactive effects of plasminogen activators including tPA or uPA given at standard clinical dosages.

* * * * *

UNITED STATES PATENT AND TRADEMARK OFFICE
CERTIFICATE OF CORRECTION

PATENT NO. : 7,271,143 B1  Page 1 of 1
APPLICATION NO. : 10/386777
DATED : September 18, 2007
INVENTOR(S) : Higazi It is certified that error appears in the above-identified patent and that said Letters Patent is hereby corrected as shown below:

Title Page:
Item (63), change "PCT/US02/02007" to --PCT/US02/20077--.

Column 1:
Line 13, change "US02/02007" to --US02/20077--.

Signed and Sealed this

Second Day of December, 2008

JON W. DUDAS
*Director of the United States Patent and Trademark Office*